United States Patent
Yokoyama et al.

Patent Number: 5,182,339
Date of Patent: Jan. 26, 1993

[54] PYRAZOLOAZOLEAZOMETHINE DYES

[75] Inventors: Shigeki Yokoyama; Tadahisa Sato; Keizo Kimura; Nobuo Furutachi; Osamu Takahashi, all of Kanagawa, Japan

[73] Assignee: Fuji Photo Film Co., Ltd., Kanagawa, Japan

[21] Appl. No.: 622,466

[22] Filed: Dec. 5, 1990

Related U.S. Application Data

[62] Division of Ser. No. 475,069, Feb. 5, 1990, Pat. No. 5,026,867, which is a division of Ser. No. 130,489, Dec. 9, 1987, Pat. No. 4,921,968.

[30] Foreign Application Priority Data

Dec. 9, 1986 [JP] Japan .................. 61-292751

[51] Int. Cl.⁵ .................. C07D 487/04; C08F 265/02; C08F 265/04
[52] U.S. Cl. .................. 525/242; 548/251; 548/110; 548/111; 548/159; 548/360.1; 548/363.1; 548/303.1; 548/360.5; 548/302.1; 544/333
[58] Field of Search .................. 525/242

[56] References Cited

U.S. PATENT DOCUMENTS

| | | | |
|---|---|---|---|
| 3,061,432 | 10/1962 | Menzel et al. | 96/55 |
| 3,725,067 | 4/1973 | Bailey et al. | 96/56.5 |
| 4,500,630 | 2/1985 | Sato et al. | 430/386 |
| 4,540,654 | 9/1985 | Sato et al. | 430/381 |
| 4,621,046 | 11/1986 | Sato et al. | 430/381 |

FOREIGN PATENT DOCUMENTS 3605279 8/1986 Fed. Rep. of Germany .
60-186667 9/1985 Japan .

OTHER PUBLICATIONS

Research Disclosure Jun. 1984 24230.
Patent Abstracts of Japan, vol. 10, No. 36 (C-328) [2093,] Feb. 13, 1986; JP-A-60 186 567 (Fuji Shashin Film K.K.) Sep. 24, 1985.

Primary Examiner—James J. Seidleck
Assistant Examiner—Vasu S. Jagannathan
Attorney, Agent, or Firm—Sughrue, Mion, Zinn, Macpeak & Seas

[57] ABSTRACT

A pyrazoloazoleazomethine dye represented by formula (I)

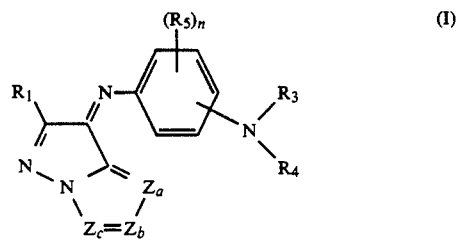

wherein, $R_1$ represents a substituent having a Hammett's substituent constant value of at least 0.6; $Z_a$, $Z_b$, and $Z_c$ each represents

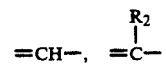

(wherein $R_2$ represents a hydrogen atom or a substituent), or $=N-$; when $Z_c=Z_b$ is a carbon-carbon double bond, it may form a part of an aromatic ring; $R_3$, $R_4$, and $R_5$ each represents a hydrogen atom or a substituent; and n represents 1 or 2; said dye may form a dimer or higher polymer by combining with each other or to a polymer through a divalent or higher valent group at $R_1$, $Z_a$, $Z_b$, or $Z_c$.

12 Claims, 2 Drawing Sheets

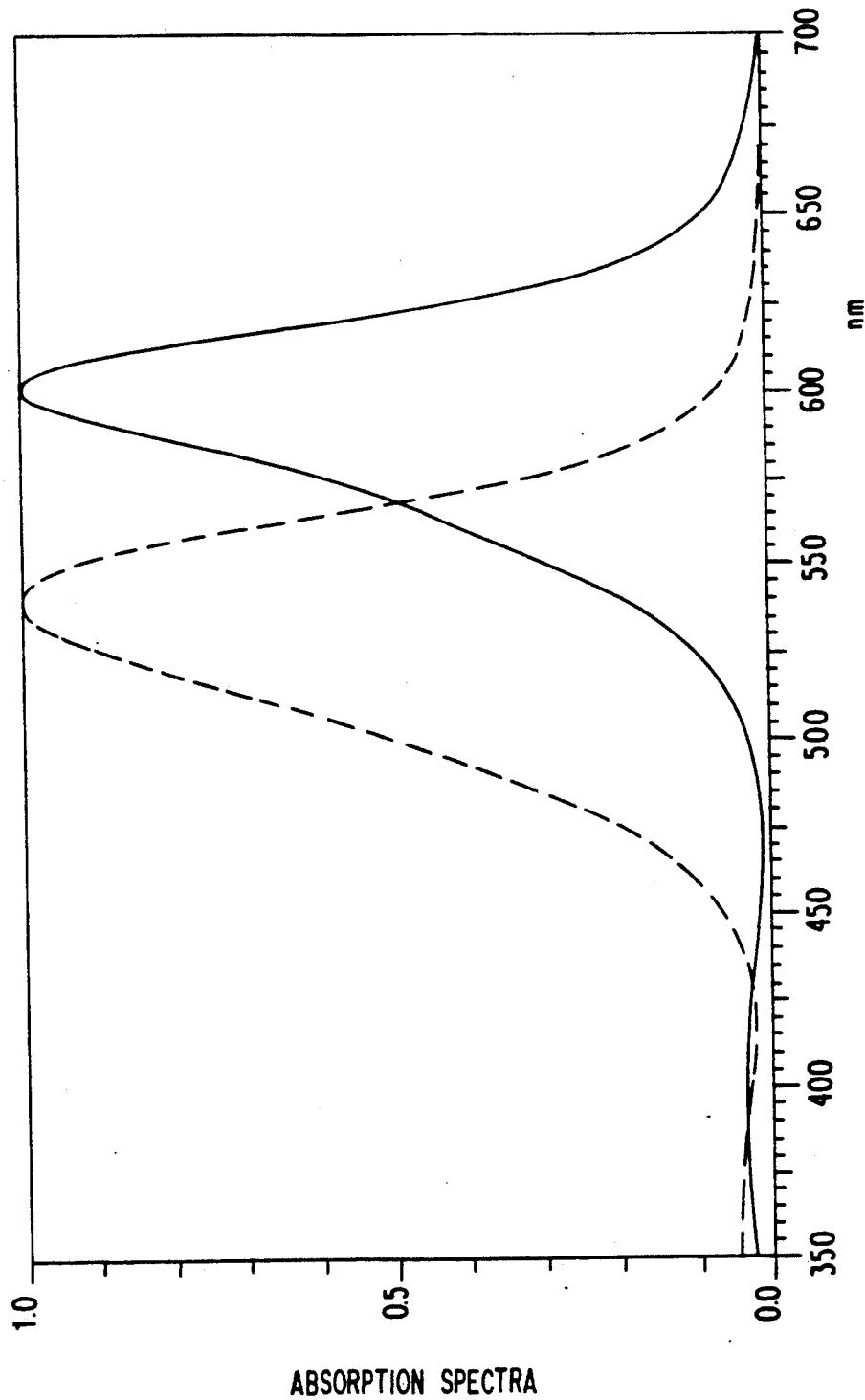

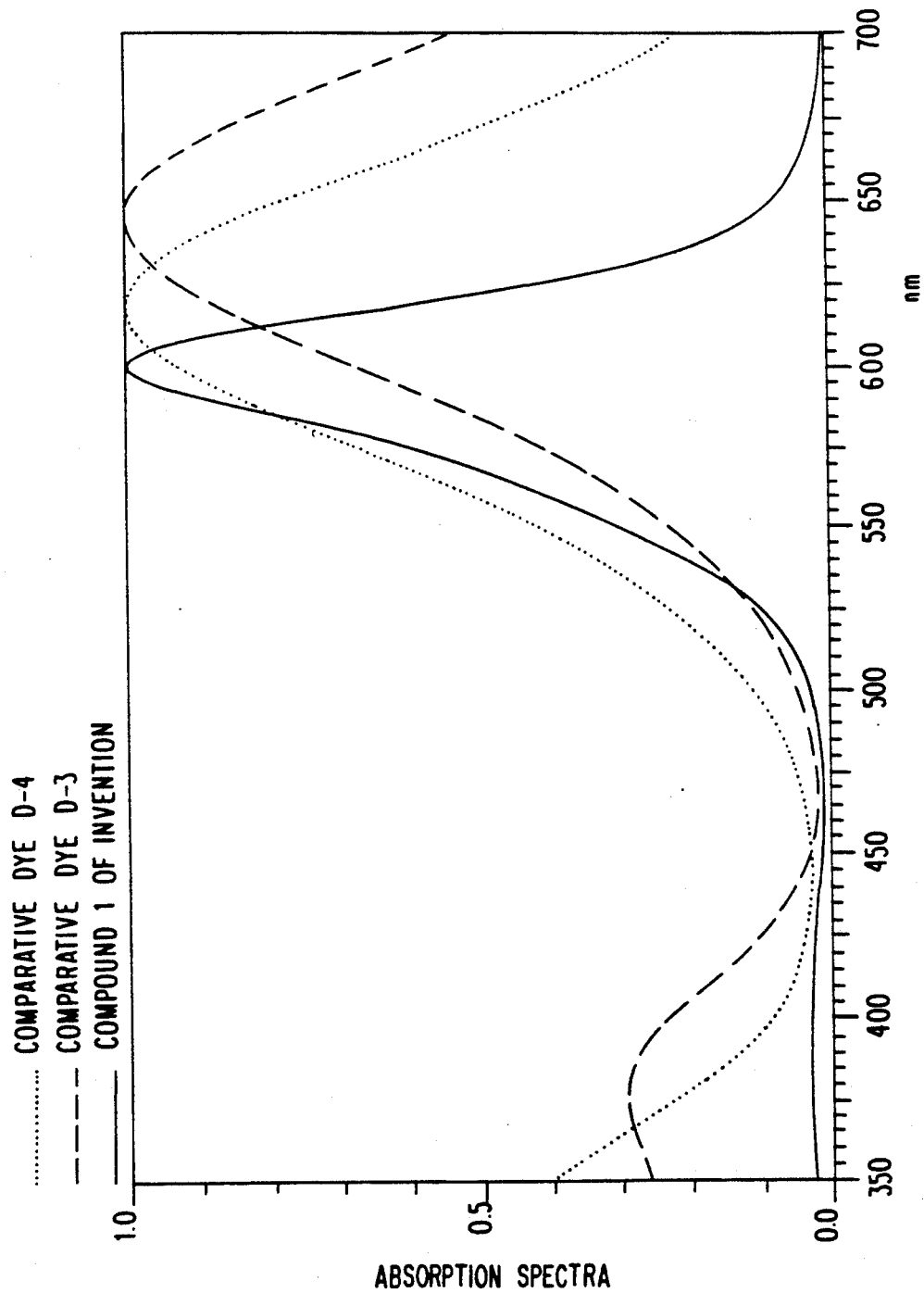

PYRAZOLOAZOLEAZOMETHINE DYES

This is a divisional of application Ser. No. Q7/475,069 filed Feb. 5, 1990 (U.S. Pat. No. 5,026,867) which is a divisional of application Ser. No. 130,489, filed Dec. 9, 1987 (U.S. Pat. No. 4,921,968).

FIELD OF THE INVENTION

This invention relates to novel pyrazoloazoleazomethine dyes, and more particularly to novel pyrazoloazoleazomethine dyes having improved hue and molecular extinction coefficient.

BACKGROUND OF THE INVENTION

Known pyrazoloazoleazomethine dyes include various dyes obtained by the coupling reaction of 1H-pyrazolo[1,5-a]benzimidazoles disclosed, e.g., in U.S. Pat. No. 3,061,432, 1H-pyrazolo[1,5-c]-1,2,4-triazoles disclosed, e.g., in U.S. Pat. No. 3,725,067, 1H-imidazo[1,2-b]pyrazoles disclosed, e.g., in U.S. Pat. No. 4,500,630, 1H-pyrazolo[1,5-b]-1,2,4-triazoles disclosed, e.g., in U.S. Pat. No. 4,540,654, 1H-pyrazolo[1,5-d]tetrazoles disclosed, e.g., in Japanese Patent Application (OPI) No. 33552/85 (the term "OPI" as used herein means an "unexamined published patent application"), or 1H-pyrazolo[1,5-b]pyrazoles disclosed, e.g., in Japanese Patent Application (OPI) No. 43659/85 with the oxidation product of an aromatic primary amine color developing agent for photography in the existence of an alkali.

It is disclosed in the above described patents and Japanese Patent Application (OPI) No. 186567/85 that pyrazoloazoleazomethine dyes can be utilized as, in particular, image-forming magenta dyes for silver halide color photographic materials by utilizing the above-described coupling reaction.

While pyrazoloazoleazomethine dyes which are utilized as magenta dyes for conventional silver halide color photographic materials have, in addition to main absorptions, harmful side absorptions at the shorter wavelength side of the main absorptions, the above-described pyrazoloazoleazomethine dyes have less side absorptions and hence give clearer hue as compared to the pyrazoloazoleazomethine dyes.

Also, some pyrazoloazoleazomethine dyes, e.g., pyrazolo[5,1-c]-1,2,4-triazoleazomethine dyes disclosed in U.S. Pat. No. 3,725,067, pyrazolo[1,5-b]-1,2,4-triazoloazomethine dyes disclosed in U.S. Pat. No. 4,540,654, and pyrazolo[1,5-d]-tetrazoleazomethine dyes disclosed in Japanese Patent Application (OPI) No. 33552/85 give sharp visible absorption spectra as compared to conventional pyrazoloazoleazomethine dyes, and hence give clearer hue as well as lower side absorption described above.

However, with recent requirements for further improving the image quality of silver halide color photographic materials, dyes which can give sharper absorption spectra and have clearer hue than the above-described pyrazoloazoleazomethine dyes have been desired.

Also, the molecular extinction coefficient of the pyrazoloazoleazomethine dyes described above is at most $6 \times 10^4$ l.mol$^{-1}$.cm$^{-1}$, and hence dyes having a higher molecular extinction coefficient have been desired.

Dyes having a higher molecular extinction coefficient can give a desired optical density with a less amount thereof, and hence when these dyes are utilized as, for example, dyes for forming color images of silver halide color photographic material, the thickness of emulsion layer(s) of the color photographic material can be greatly reduced, to thus reduce the cost for the silver halide in such photographic materials, and furthermore, such silver halide photographic materials provide images having improved sharpness.

SUMMARY OF THE INVENTION

An object of this invention is, therefore, to provide novel pyrazoloazoleazomethine dyes having sharp visible absorption spectra and clear color.

A second object of this invention is to provide novel pyrazoloazoleazomethine dyes having a high molecular extinction coefficient and providing a desired optical density with less amount thereof.

A third object of this invention is to provide novel pyrazoloazoleazomethine dyes having absorption at a longer wavelength region.

As a result of various investigations for obtaining pyrazoloazoleazomethine dyes capable of attaining the above-described objects, the inventors have discovered that when a specific strong electron attractive group is introduced into a substituent of the pyrazoloazole skeleton of a pyrazoloazoleazomethine dye, the visible absorption spectrum of the dye becomes sharper and the dye provides a clearer hue as well as the molecular extinction coefficient of the dye reached as high as $9 \times 10^4$ l.mol$^{-1}$.cm$^{-1}$, and that when a specifically strong electron attractive group is introduced into the pyrazoloazole skeleton of the dye, the maximum absorption wavelength of the absorption spectrum of the dye is greatly shifted to deep color side and dye becomes a blue or cyan dye having the maximum absorption wavelength of over 600 nm by suitably selecting the pyrazoloazole skeleton and the specifically strong electron attractive group, while a conventional pyrazoloazoleazomethine dye is a red, magenta, or purple dye having the maximum absorption wavelength at the region of from about 520 to about 570 nm, and have succeeded in accomplishing the present invention.

That is, the invention provides a pyrazoloazoleazomethine dye represented by formula (I)

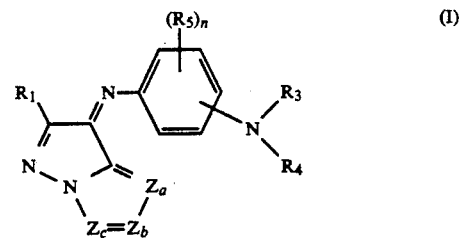

(I)

wherein $R_1$ represents a substituent having a Hammett's substituent constant $\nu_p$ value of at least 0.6, preferably from 0.6 to 2.0, most preferably from 0.6 to 1.0; Za, Zb, and Zc each represents

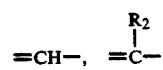

(wherein $R_2$ represents a hydrogen atom or a substituent), or =N—; when Zc=Zb forms a carbon-carbon double bond, it may form a part of an aromatic ring; $R_3$, $R_4$, and $R_5$ each represents a hydrogen atom or a substituent; and n represents a number of $R_5$ and it represents 1 or 2; said dye may form a dimer (including a biscompound) or higher polymer at $R_1$, $Z_a$, $Z_b$, or $Z_c$ through a divalent or higher valent group by combining with each other or to a polymer.

BRIEF DESCRIPTION OF THE DRAWINGS

FIG. 1 is a graph showing visible absorption spectra of the pyrazoloazoleazomethine dye of this invention in Example 2 and a comparison pyrazoloazoleazomethine dye in Example 2, and FIG. 2 is a graph showing visible absorption spectra of the pyrazoloazoleazomethine dye and cyan dyes formed from comparison phenolic cyan couplers in Example 4.

DETAILED DESCRIPTION OF THE INVENTION

Detailed descriptions with respect to $R_1$, $R_3$, $R_4$ and $R_5$ can be seen in the descriptions for corresponding groups in formula (II) to (VII).

The pyrazoloazoleazomethine dyes of this invention represented by formula (I) described above are preferably pyrazoloazoleazomethine dyes represented by formula (II), (III), (IV), (V), (VI), or (VII).

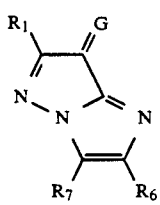
(II)

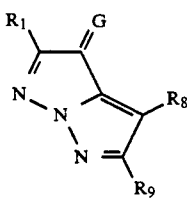
(III)

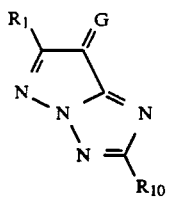
(IV)

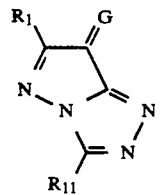
(V)

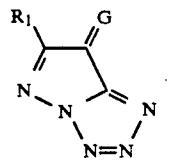
(VI)

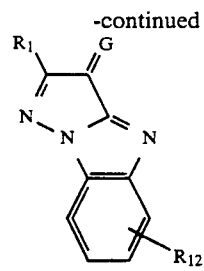
(VII)

In formula (II) to (VII), G is a structural moiety derived from an aromatic primary amine and is by formula (VIII)

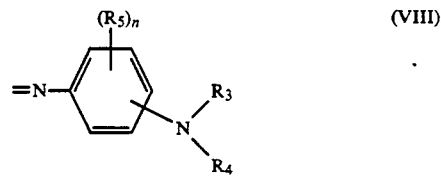
(VIII)

wherein $R_3$, $R_4$, $R_5$, and n have the same meanings as defined above for formula (I); and $R_3$ and $R_4$ each preferably represents a hydrogen atom or an alkyl group and $R_5$ preferably represents a hydrogen atom, a halogen atom, or an alkyl group. When $R_5$ is a halogen atom or an alkyl group it is preferable that $R_5$ and

are at the o- and p-position, respectively, of the benzene ring from the point of view of the absorbance and hue of the dye.

In formula (II) to (VII), $R_1$ has the same meanings as defined above for formula (I), and $R_6$, $R_7$, $R_8$, $R_9$, $R_{10}$, $R_{11}$, and $R_{12}$ each represents a hydrogen atom or a substituent. The compound represented by formula (VII) may have plural groups represented by $R_{12}$.

The pyrazoloazoleazomethine dyes of this invention are more preferably the pyrazoloazoleazomethine dyes shown by formula (IV), (V), or (VI), and further preferably those shown by formula (IV) described above.

Examples of groups shown by $R_6$, $R_7$, $R_8$, $R_9$, $R_{10}$, $R_{11}$, and $R_{12}$ in formula (II) to (VII) described above include a hydrogen atom, a halogen atom, a saturated or unsaturated hydrocarbon group, an aryl group, a heterocyclic group, a cyano group, an alkoxy group, an aryloxy group, an acylamine group, an anilino group, a ureido group, a sulfamoylamino group, an alkylthio group, an arylthio group, an alkoxycarbonylamino group, a sulfonamido group, a carbamoyl group, a sulfamoyl group, a sulfonyl group, an alkoxycarbonyl group, a heterocyclic oxy group, an acyloxy group, a carbamoyloxy group, a silyloxy group, an aryloxycarbonylamino group, an imido group, a heterocyclic thio group, a sulfinyl group, a phosphonyl group, an aryoxycarbonyl group, an acyl group, etc.

More specifically, examples of $R_6$, $R_7$, $R_8$, $R_9$, $R_{10}$, $R_{11}$, and $R_{12}$ are a hydrogen atom a halogen atom (e.g., a chlorine atom, a bromine atom, etc.,), a saturated or unsaturated hydrocarbon group preferably having 1 to 32 carbon atoms (e.g., a straight chain or branched alkyl group, an aralkyl group, an alkenyl group, an alkynyl group, a cycloalkyl group, and a cycloalkenyl group, each of which may be substituted by a substituent which is connected thereto through an oxygen atom, a nitrogen atom, a sulfur atom, or a carbonyl group), a hydroxy group, an amino group, a nitro group, a carboxy group, a cyano group, or a halogen atom; and examples of these alkyl groups are a methyl group, a propyl group, a t-butyl group, a trifluoromethyl group, a tridecyl group, a 2-methanesulfonylethyl group, a 3-(3-pentadecylphenoxy) propyl group, a 3-{4-{2-[4-[4-hydroxyphenylsulfonyl) phenoxyl]dodecaneamido}phenyl} propyl group, a 2-ethoxytridecyl group, a trifluoromethyl group, a cyclopentyl group, a 3-(2,4-di-t-amylphenoxy)-propyl group, etc.), an aryl group (e.g., a phenyl group, a 4-t-butylphenyl group, a 2,4-di-t-amylphenyl group, a 4-tetradecanemidophenyl group, etc.), a heterocyclic group (e.g., a 5- to 7- membered heterocyclic ring having at least one of N, O and S atoms, such as a 2-furyl group, a 2-thienyl group, a 2-pyrimidinyl group, a 2-benzothiazolyl group, etc.), a cyano group, an alkoxy group, (e.g., a methoxy group, an ethoxy group, a 2-methoxyethoxy group, a 2-dodecylethoxy group, a 2-methanesulfonylethoxy group, etc.,), an aryloxy group (e.g. a phenoxy group, a 2-methylphenoxy group, a 4-t-butylphenoxy group, etc.), an acylamino group (e.g., an acetamide group, a benzamide group, a tetradecaneamido group, an α-(2,4-di-t-amylphenoxy)-butylamido group, a γ-(3-t-butyl-4-hydroxyphenoxy)-butylamido group, an α-{4-(4-hydroxyphenylsulfonyl)-phenoxy}decaneamido group, etc.), an anilino group (e.g., a phenylamino group, a 2-chloroanilino group, a 2-chloro-5-tetradecaneamidoanilino group, a 2-chloro-5-dodecyloxycarbonylanilino group, an N-acetylanilino group, a 2-chloro-5-{α-(3-t-butyl-4-hydroxyphenoxy)dodecaneamdo}anilino group, etc.), a ureido group (e.g., a phenylureido group, a methylureido group, an N,N-butylureido group, etc.), a sulfamoylamino group (e.g., an N,N-dipropylsulfamoylamino group, an N-methyl-N-decylsulfamoylamino group, etc.), an alkylthio group (e.g., a methylthio group, an octylthio group, a tetradecylthio group, a 2-phenoxyethylthio group, a 3-phenoxypropylthio group, a 3-(4-t-butylphenoxy) propylthio group, etc.), an arylthio group (e.g., a phenylthio group, a 2-butoxy-5-t-octylphenylthio group, a 3-pentadecylphenylthio group, a 2-carboxyphenylthio group, a 4-tetradecaneamidophenylthio group, etc.), an alkoxycarbonylamion group (e.g., a methoxycarbonylamino group, a tetradecyloxycarbonylamino group, etc.), a sulfonamido group (e.g., a methanesulfonamido group, a hexadecanesulfonamido group, a benzenesulfonamido group, a p-toluenesulfonamido group, an octadecanesulfonamido group, a 2-methyloxy-5-t-butylbenzenesulfonamido group, etc.), a carbamoyl group (e.g., an E-ethylcarbamoyl group, an N,N-dibutylcarbamoyl group, an N-(2-dodecyloxyethyl)carbamoyl group, an N-methyl-N-dodecylcaramoyl group, an N-{3-(2,4-di-t-amylphenoxy)propyl}carbamoyl group, etc.), a sulfamoyl group (e.g., an N-ethylsulfamoyl group, an N,N-dipropylsulfamoyl group, an N-(2-dodecyloxyethyl) suflamoyl group, an N-ethyl-N-dodecylsulfamoyl group, an N, N-diethyksuylfamoyl group, etc.), a sulfonyl group (e.g., a methanesulfonyl group, an octanesulfonyl group, a benzenesulfonyl group, a toluenesulfonyl group, etc.), an alkoxycarbonyl group (e.g., a methoxycarbonyl group, a butyuloxycarbonyl group, a dodecyloxycarbonyl group, an octadecyloxycarbonyl group, etc.), a heterocyclic oxy group (wherein the heterocyclic group preferably is a 5- to 7- membered heterocyclic ring having at least one of N, O and S atoms, such as a 1-phenyltetrazole-5-oxy group, a 2-tetrahydropyranyloxy group, etc.), an acyloxy group (e.g., an acetoxy group, etc.), an acylamioxy group (e.g., an acetylaminoxy group, a benzoylaminoxy group, etc.), a silyloxy group (e.g., a trimethylsilyloxy group, a dibutylmethylsilyloxy group, etc.), an aryloxycarbonylamino group (e.g., a phenoxycarbonylamino group, etc.), an imido group (e.g., an N-succinimido group, an N-phthalimido group, a 3-octadecenylsuccinimido group, etc.), a heterocyclic thio group (wherein the heterocyclic group preferably is a 5- to 7- membered heterocyclic ring having a least one of N, O and S atoms, such as a 2-benzothiazolylthio group, a 2,4-di-phenoxy-1,3,5-triazole-6-thio group, a 2-pypridylthio group, etc.), a sulfinyl group (e.g., a dodecanesulfinyl group, a 3-pentadecylphenylsulfinyl group, a 3-phenoxypropylthio group, etc.), a phosphonyl group (e.g., a phenoxyphosphonyl group, an octyloxyphosphonyl group, a phenyl phosphonyl group), an aryloxycarbonyl group (e.g., a phenoxycarbonyl group, etc.), an acyl group (e.g., an acetyl group, a 3-phenylpropanoyl group, a benzoyl group, a 4-dodecyloxybenzoyl group, etc.), etc.

In addition, when $R_1$, $R_6$, $R_7$, $R_8$, $R_9$, $R_{10}$, $R_{11}$, and $R_{12}$ in formulae (II) to (VII) described above and $R_3$, $R_4$, and $R_5$ in formula (VIII) described above are an alkyl group or an alkyl-containing group (e.g., an alkoxy group, an alkylthio group, an alkoxycarbamoyl group, an alkoxycarbonyl group, etc.), the carbon atom number of the alkyl group is usually from 1 to 50, and preferably from 1 to 40, and more preferably from 1 to 32, and when these groups an acyl group, the carbon atom number thereof is same as above.

Particular examples of groups having a Hammett's substituent constant $\sigma_p$ value of at least 0.6 are a cyano group, a nitro group, a trialkylammonium group (e.g., a trimethylammonium group, a triethylammonium group, a tributylammonium group, a trioctylammonium group, a tridecylammonium group, etc.), a triarylammonium group (e.g., a triphenylammonium group, a tritolylammonium group, etc.), a dialkylsulfonium group, (e.g., a dimethylsulfonium group, a diethylsulfonium group, etc.), a diarylsulfonium group (e.g., a diphenylsulfonium group, etc.), a perfluoroalkylsulfinyl group (e.g., a trifluoromethylsulfinyl group, a pentfluoroethylsulfinyl group, a heptafluoropropylsulfinyl group, a perfluorooctylsulfinyl group, etc.), an ω-hydroperfluoroalkylsulfinyl group (e.g., an ω-hydroperfluorooctyl-sulfinyl group, an ω-hydroperfluorododecylsulfinyl group, etc.), an alkanesulfonyl group (e.g., methanesulfonyl group, difluoromethanesulfonyl group, a trifluoromethanesulfonyl group, a dichloromethanesulfonyl group, an ethanesulfonyl group, a propanesulfonyl group, an octanesulfonyl group, a decanesulfonyl group, a pentafluoroethanesulfonyl group, a heptafluoropropanesulfonyl group, a perfluorooctanesulfonyl group, an ω-hydroperfluorooctanesulfonyl group, etc.), an arylsulfonyl group, (e.g., a phenylsulfonyl group, a tolysulfonyl, group, a pentafluorophenylsulfonyl group, etc.), a β-carboxyvinyl group, a β,β-dicyanovinyl group, etc. These groups may be those represented by $R_1$, $R_6$, $R_7$, $R_8$, $R_9$, $R_{10}$, $R_{11}$, and $R_{12}$.

These examples are further described, for example, in C. Hansch et al., *Substituent Constants For Correlation Analysis in Chemistry and Biology*, John Wiley & Sons, N.Y. (1979), C. Hansch et al., *Journal of Medicinal Chemistry*, Vol. 16, pp. 1207-1216 (1973), C. Hansch et al., ibid, Vol. 20, pp. 304-306 (1977), etc.

However, it is not unusual that different values are reported by different reporters for the same substituent, and in that case it is preferred to use values described in the last two references (both, C. Hansch et al) listed above. Further with respect to substituents which are not described in the above references, measurement can be performed in accordance with the definition described in L. P. Hammett, *Physical Organic Chemistry*, (McGraw-Hill, 1970).

Furthermore, $R_1$, $R_6$, $R_7$, $R_8$, $R_9$, $R_{10}$, $R_{11}$, or $R_{12}$ in formulae (II) to (VII) can be, divalent group forming a bis-compound. Examples of such a divalent group are a substituted or unsubstituted alkylene group (the alkylene group includes group having at least one oxygen atom in the hydrocarbon chain; e.g., a methylene group, an ethylene group, a 1,10-decylene group, $-CH_2CH_2-O-CH_2CH_2-$, etc.), a substituted or unsubstituted phenylene group (e.g., a 1,4-phenylene group, a 1,3-phenylene group,

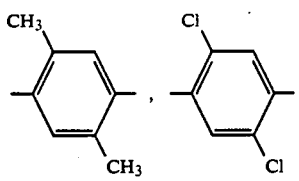

etc.), —NHCO—$L_1$— CONH (wherein $L_1$ represents a substituted or unsubstituted alkylene or phenylene group, e.g.,

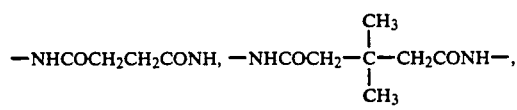

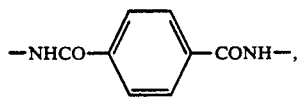

—S—$L_2$—S— group (wherein $L_2$ represents a substituted or unsubstituted alkylene group, e.g.,

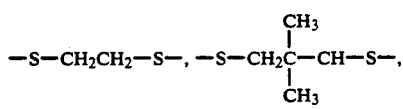

etc.), etc.

The pyrazoloazoleazomethine dye of this invention represented by formula (II) to (VII) described above may be a polymer wherein the dye is bonded to a polymer main chain through $R_1$, $R_6$, $R_7$, $R_8$, $R_9$, $R_{10}$, $R_{11}$, or $R_{12}$ as a divalent linkage group.

Such a divalent linkage group includes an alkylene group (substituted or unsubstituted alkylene group, such as a methylene group, an ethylene group, a 1,10-decylene group, $-CH_2CH_2OCH_2CH_2-$, etc.) a phenylene group (substituted or unsubstituted phenylene group, such as a 1,4-phenylene group, a 1,3-phenylene group,

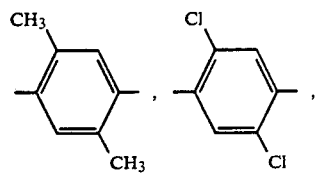

etc.), —NHCO—, —COHN—, —O—, —OCO—, and aralkylene group (e.g.

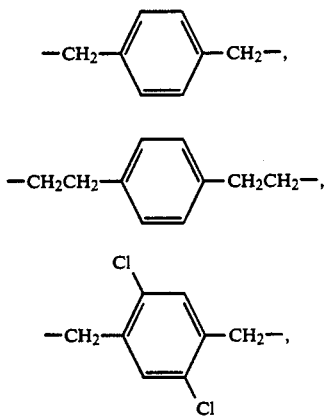

etc.) a group formed by combining the groups selected therefrom.

Preferred examples of the linkage group are

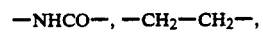

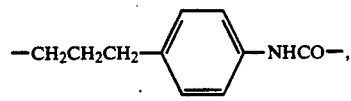

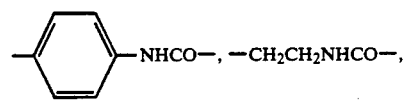

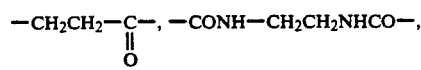

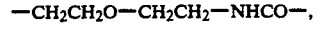

and

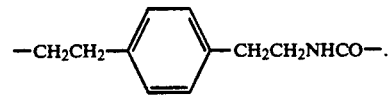

When the pyrazoloazoleazomethine dye represented by formula (II) to (VII) described above is a polymer, it may be a copolymer with an ethylenically unsaturated monomer such as styrene, methyl acrylate, ethyl acylate, butyl methacrylate, acrylic acid, acrylamide, etc.

The non-coloring ethylenically unsaturated monomer for forming a copolymer with the solid water-insoluble monomer, pyrazoloazole can be selected so that the copolymer formed has desired physical and/or chemical properties such as solubility, compatibility with a binder for the dye composition, flexibility, heat-stability, etc.

The polymeric pyrazoloazoleazomethine dye of this invention may be water-soluble or water-insoluble, but is particularly preferably a polymer latex.

Preferred synthesis intermediates for producing the pyrazoloazoleazomethine dyes of this invention shown by formula (II) to (VII) described above are pyrazoloazoles represented by following formulae (IIA) to (VIIA):

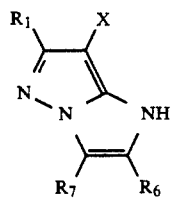
(IIA)

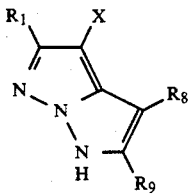
(IIIA)

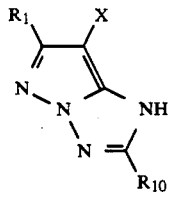
(IVA)

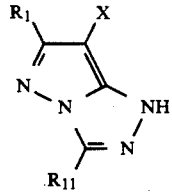
(VA)

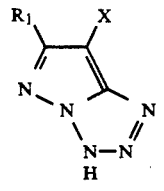
(VIA)

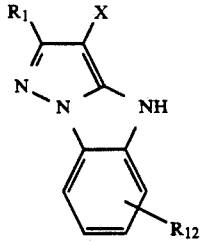
(VIIA)

In formulae (IIA) to (VIIA), $R_1$ and $R_6$ to $R_{12}$ have the same meanings as defined above and X represents a hydrogen atom, a halogen atom, or a group capable of releasing by a coupling reaction with the oxidation product of an aromatic primary amino compound. (With respect to such a group capable of releasing, detailed descriptions can be seen in, for example, U.S. Pat. No. 4,540,654, column 4, line 30 to column 5, line 24.)

These synthesis intermediates as described above can be produced by the methods disclosed, for example, in U.S. Pat. Nos. 3,061,432, 3,725,067, 4,500,630, and 4,540,654, Japanese Patent Application (OPI) Nos. 33552/85, 43659/85, and 186567/85.

The pyrazoloazoleazomethine dyes of this invention represented by formulae (II) to (VII) can be produced by oxidative-coupling the synthesis intermediates shown by formulae (IIA) to (VIIA) and an aromatic primary amine represented by formula (VIIIA)

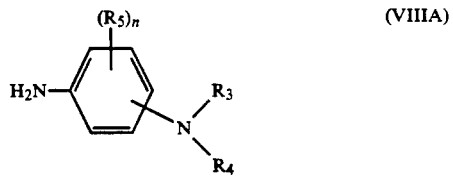
(VIIIA)

wherein $R_3$ and $R_4$, which may be the same or different, each represents a hydrogen atom or an alkyl group, which may have a substituent, $R_5$ represents a hydrogen atom, a halogen atom, or an alkyl group, which may have a substituent; and n represents a number of substituents of $R_5$ which is 1 or 2; when n is 2, said $R_5$ groups may be the same or different.

The amine represented by formula (VIIIA) described above can be used as a salt with a mineral acid or an organic acid and in this case the air oxidation can be easily prevented and the dissolution rate of the compound can be improved.

In formula (VIIIA), $R_3$ and $R_4$ preferably represent a hydrogen atom, an alkyl group or a substituted alkyl group such as hydroxyalkyl group, an alkoxyalkyl group, an alkoxyalkoxyalkyl group, and an alkysulfonamidoalkyl group, and $R_5$ may represents an alkyl group substituted with an alkoxy group or a halogen atom.

Furthermore, examples of the alkyl group in the phenylenediamine derivatives shown by formula (VIIIA) described above and the alkyl moiety of the alkoxy group and the substituted alkyl group are lower alkyl groups having from 1 to 4 carbon atoms, such as methyl, ethyl, n-propyl, iso-propyl, n-butyl, iso-butyl, sec-butyl, t-butyl, etc., and higher alkyl groups having from 5 to 18 carbon atoms, such as n-amyl, dl-2-methyl-1-butyl, iso-amyl, sec-amyl, t-amyl, n-hexyl, methylamyl, 2-ethylbutyl, n-heptyl, 2-heptyl, 3-heptyl, n-octyl, 2-octyl, 2-ethylhexyl, n-dodecyl, n-octadecyl, cyclohexyl, etc., which include straight chain, branched or cyclic alkyl groups.

Examples of a halogen atom are a chlorine atom, a bromine atom, and an iodine atom.

The aromatic primary amine shown by formula (VIIIA), which are used for producing the pyrazoloazoleazomethine dyes of this invention are preferably ortho- or para-pheynlenediamines, and more preferably para-phenylene-diamines. Specific examples thereof are those having N-alkyl group, such as:

D 1) 4-amino-N-ethylaniline,
D 2) 4-amino-N,N-diethylaniline,
D 3) 4-amino-3-methyl-N,N-diethylaniline, etc.;
those having N-hydroxyalkyl group such as
D 4) 4-amino-N-ethyl-N-(β-hydroxyethyl)aniline, D 5) 4-amino-3-methyl-N-ethyl-N-(β-hydroxyethyl)aniline, etc;

those having N-alkoxyalkyl group such as

D 6) 4-amino-3-methyl-N-ethyl-(β-methoxyethyl)aniline,

D 7) 4-amino-3-methyl-N-ethyl-N-methoxybutyl)aniline,

D 8) 4-amino-3-methyl-N-ethyl-N-(β-ethoxyethyl)aniline,

D 9) 4-amino-3-propyl-N-ethyl-N-(β-methoxyethyl)aniline,

D 10) 4-amino-3-propyl-N-ethyl-N-(β-methoxyethyl)aniline,

D 11) 4-amino-3-methoxy--N-ethyl-N-(β-methoxyethyl)aniline,

D 12) 4-amino-3-methyl-N-ethyl-N-(β-butoxyethyl)aniline, etc.;

those having N-alkoxyalkoxyalkyl group such as

D 13) 4-amino-3-ethyl-N-ethyl-N-[β-(β-methoxyethoxy)ethyl]aniline,

D 14) 4-amino-3-methyl-N-ethyl-N-[β-(β-ethoxyethoxy)ethyl]aniline,

D 15) 4-amino-3-methyl-N-ethyl-N-[β-(β-butoxyethoxy)ethyl]aniline,

D 16) 4-amino-3-methyl-N-methyl-N-[β-(β-ethoxyethoxy)ethyl]aniline,

D 17) 4-amino-N-ethyl-N-[β-(β-methoxyethoxy)ethyl]aniline,

D 18) 4-amino-N-ethyl-N-[β-(β-ethoxyethoxy)ethyl]aniline, etc.; and those having N-alkysulfonamidoalkyl group such as D 19) 4-amino-N-ethyl-N-(β-methanesulfonamidoethyl)aniline, D 20) 4-amino-3-methyl-N-ethyl-N-(β-methanesulfonamidoethyl]aniline, D 21) 4-amino-3-chloro-N-ethyl-N-(β-methanesulfonamidoethyl]aniline, D 21) 4-amino-N-ethyl-N-(β-methylfonamidoethyl)-3,5-xylidine, etc.

As the salts of the phenylenediamine derivatives, there are inorganic salts, i.e., mineral acid salts such as hydrochlorides, sulfates, nitrates, phosphates, carbonates, and hydrohalogenic acid salts such as hydrochlorides, hydrobromides, hydroiodides, etc., and organic salts such as aliphatic carboxylates such as formates, acetates, propinates, etc., aromatic carboxylates such as benzoate naphthalene-α-carboxylates, naphthalene-β-carboxylates, etc., aliphatic sulfonates such as methanesulfonates, etc., and aromatic sulfonates such as naphthalene-α-sulfonates, naphthalene-β-sulfonates, p-toluenesulfonates, etc.

They may be properly selected according to the production conditions for the dyes. For example, in the case of using the salts as photographic color developing agents, it is preferred to use the salts having no adverse influences on the photographic properties. For this purpose, the phenylenediamine derivatives are usually used as the mineral acid salts such as sulfates or aromatic sulfonates such as p-toluenesulfonates, etc.

As the phenylenediamines for use in this invention, the above-described compounds D 3), D 5), D 6), D 19) and D 20) are particularly preferred from the view point of providing particularly good hue. Also, as the substituent at the 3-position is useful for controlling the coupling speed, an electron attractive group such as chlorine atom, etc., has a function of increasing the coupling speed, and an electron donative substituent such as methyl group, etc., has a function of delaying the coupling speed.

Preferred examples of the pyrazoloazoleazomethine dyes of this invention are illustrated below but the invention is not limited to these compounds.

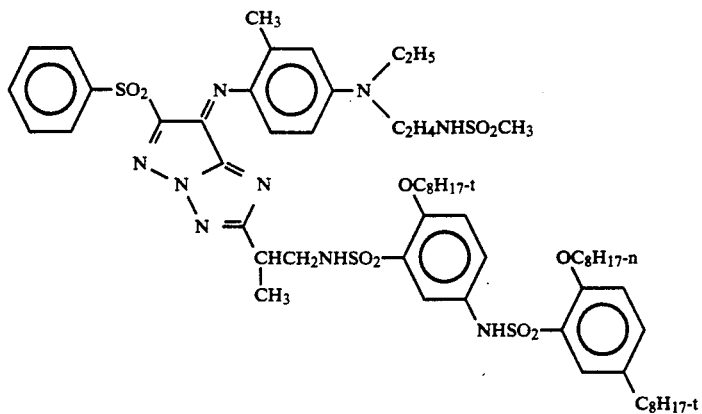

Compound 1

-continued
Compound 2
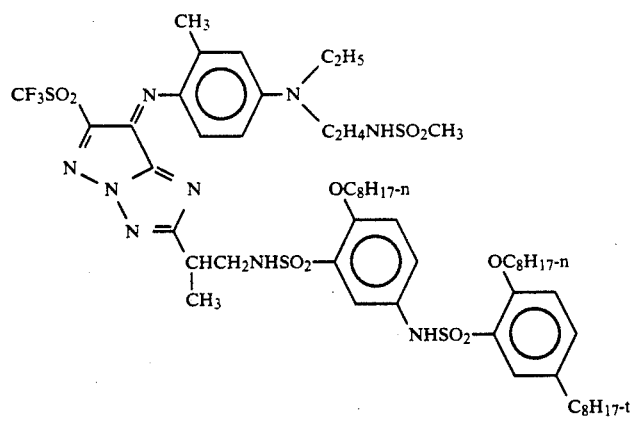
Compound 3
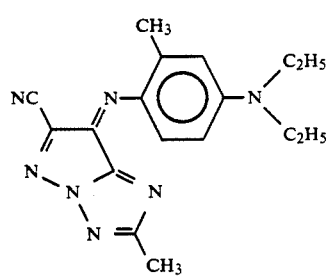
Compound 4
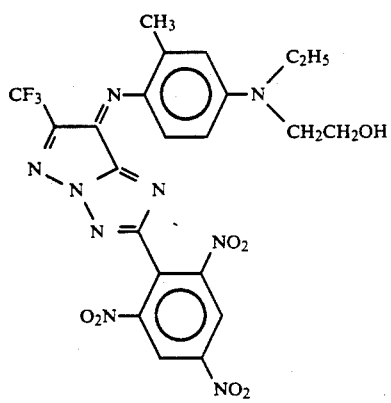
Compound 5
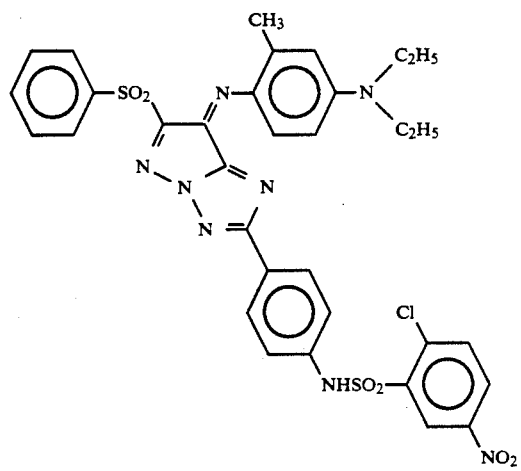

-continued
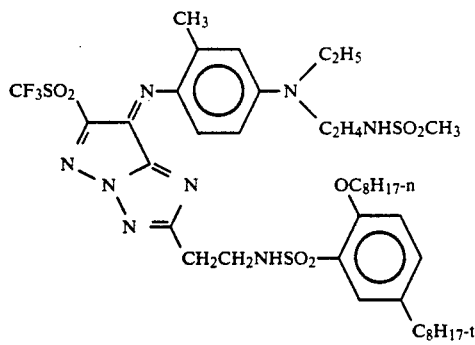
Compound 6
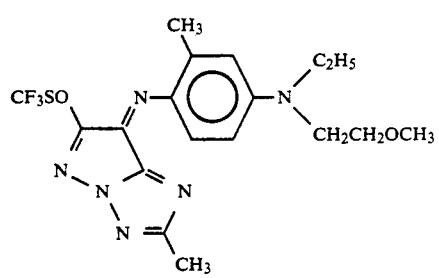
Compound 7
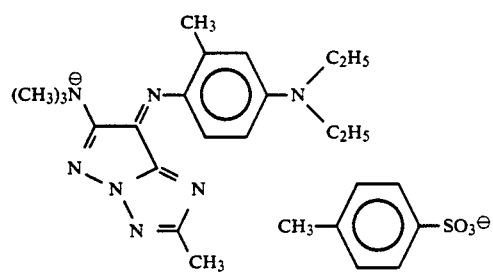
Compound 8
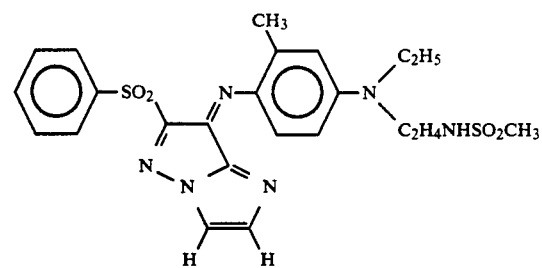
Compound 9
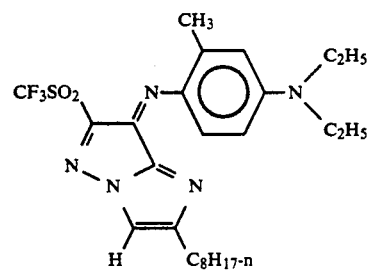
Compound 10

-continued
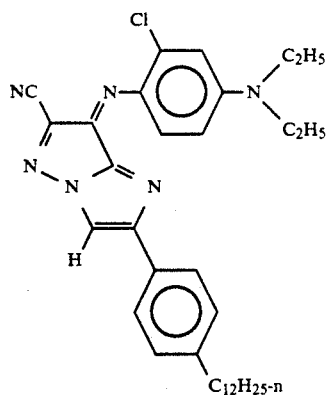
Compound 11
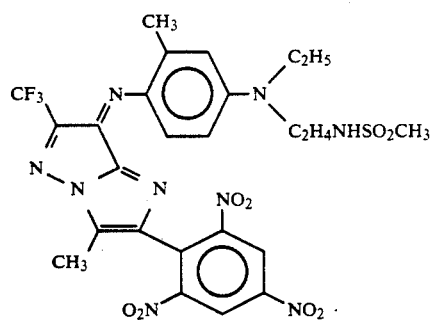
Compound 12
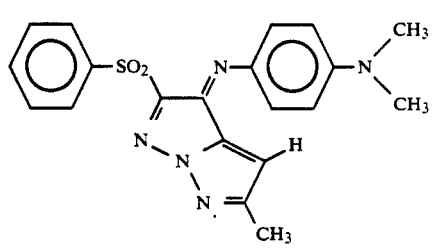
Compound 13
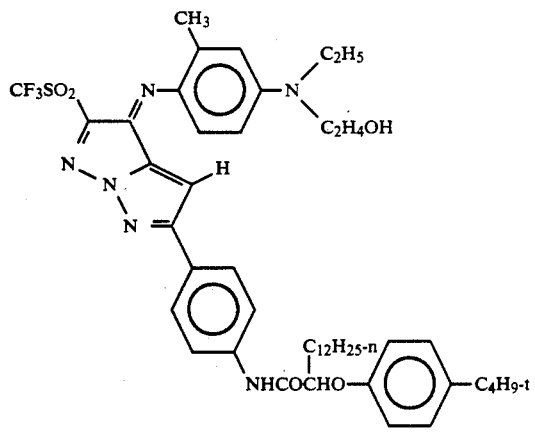
Compound 14

Compound 15
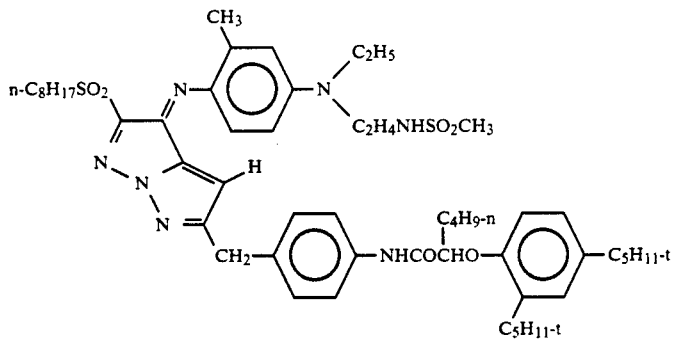
Compound 16
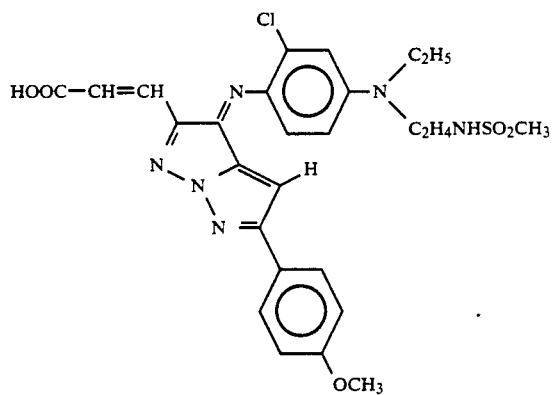
Compound 17
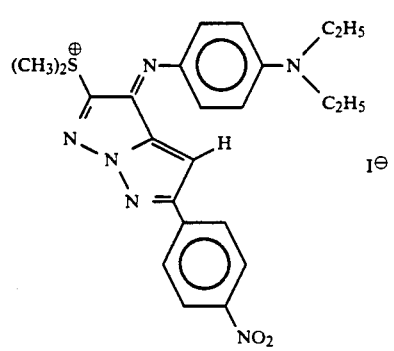
Compound 18
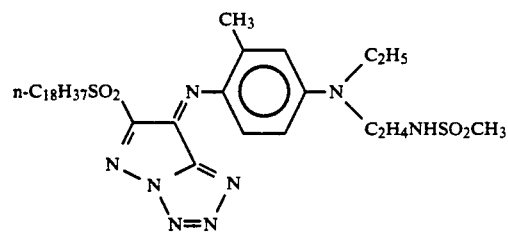
Compound 19
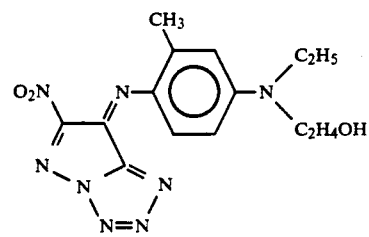

-continued
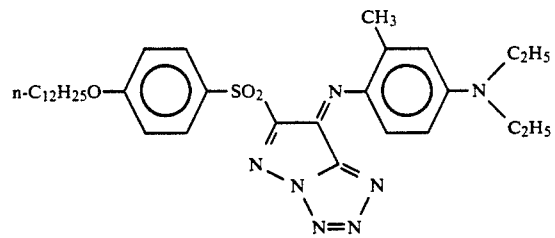
Compound 20
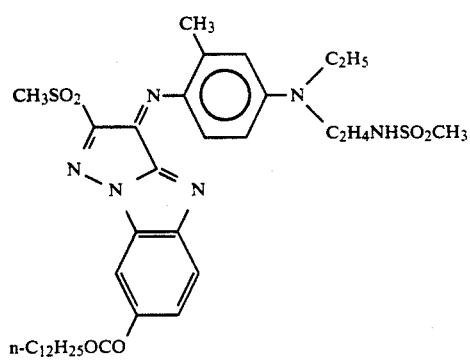
Compound 21
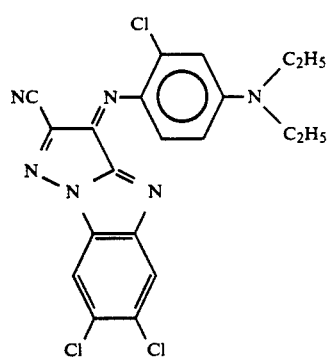
Compound 22
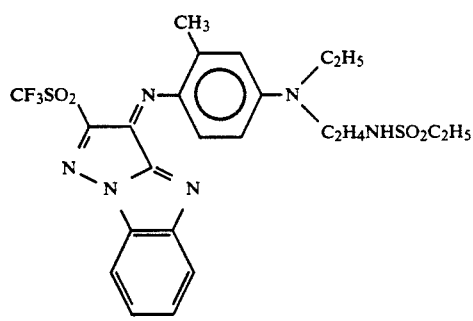
Compound 23
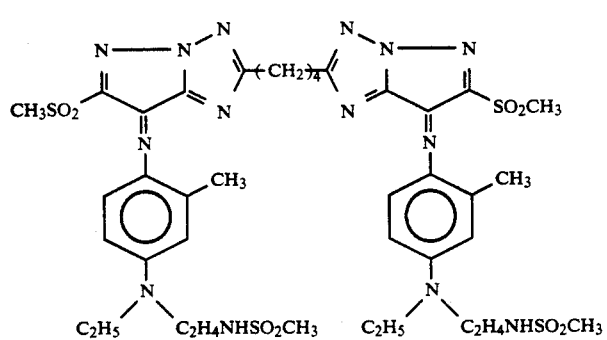
Compound 24

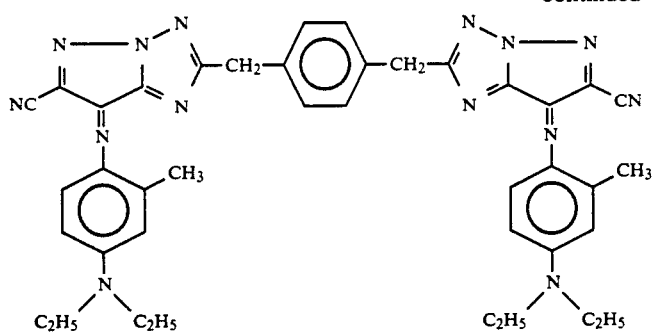

Compound 25

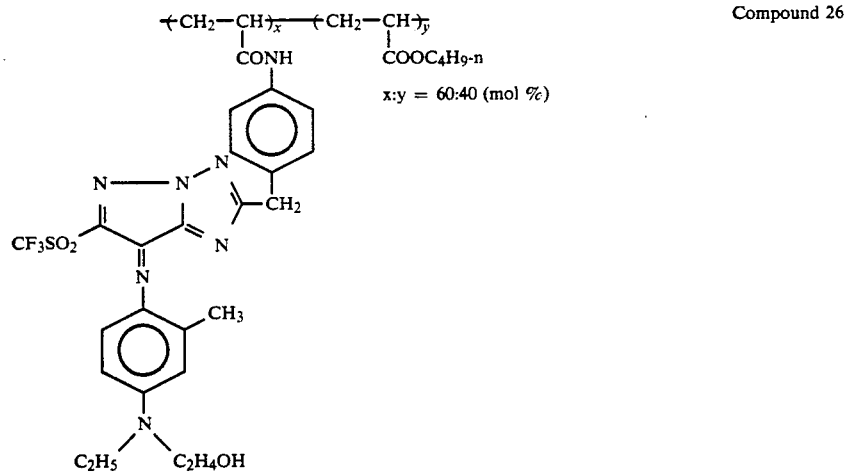

Compound 26

The Hammett's substituent constant $\sigma_p$ values of the substituents in the above-described compounds are shown in Table 1 below.

TABLE 1

| Group | $\sigma_p$ |
|---|---|
| —SO$_2$CH$_3$ | 0.72 |
| —NO$_2$ | 0.78 |
| —SO$_2$CF$_3$ | 0.93 |
| 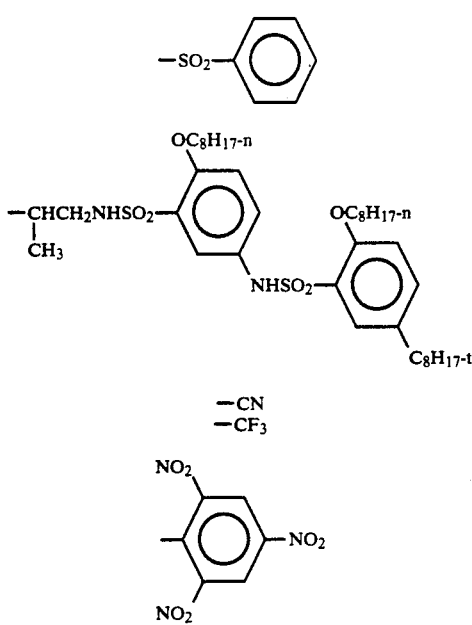 | 0.70 |
|  | −0.15 |
| —CN | 0.66 |
| —CF$_3$ | 0.54 |
|  | 0.30 |

TABLE 1-continued

| Group | $\sigma_p$ |
|---|---|
| —SOCF$_3$ | 0.69 |
| —N$^\oplus$(CH$_3$)$_3$ | 0.82 |
| —CH$_3$ | −0.17 |
| —CH=CH—COOH | 0.90 |
| —S$^\oplus$(CH$_3$)$_2$ | 0.90 |

In the pyrazoloazoleazomethine dyes of this invention, as the $\sigma_p$ value of the aforesaid substituent R$_1$ is at least 0.6 and larger, the dyes have a tendency of shifting to the deep color side. The shifting extent of $\lambda_{max}$ depends on the kind of the pyrazoloazole skeleton (formula (II) to (VI)) and on the $\sigma_p$ value of the substituent, but is generally in the range of from about 50 n.m. to 100 n.m.

The pyrazoloazoleazomethine dyes shown by formula (II) to (VII) can be synthesized in the presence of the pyrazoloazole couplers shown by formula (IIA) to (VIIA) described above, the phenylenediamine shown by formula (VIIIA) described above, and an oxidizing agent. It is considered that in the coupling reaction, the azomethine dye is formed after forming a leuco dye by a nucleophilic attack of a coupler anion to a quinonediimine formed by the oxidation of the phenylenediamine as described in T. H. James, *The Theory of the Photographic Process*, 4th edition, Chapter 12, (1977, Macmillan). The reaction proceeds under preferably basic conditions and the reaction medium may be an organic solvent, an aqueous organic solvent, or an aqueous solution. When the reaction is proceeded in a basic aqueous solution, the coupler may be an oil drop-in water dispersion and further the dispersion may exist in a hydrophilic colloid medium such as gelatin.

Also, as the oxidizing agent, an organic or inorganic oxidizing agent having an electric potential capable of oxidizing the phenylenediamine can be used and the oxidizing agent may be dissolved in a reaction medium or may be dispersed therein.

When X in formula (II) to (VII) described above is a hydrogen atom, from 0.1 to 10 mols, and preferably from 0.5 to 2 mols of the phenylenediamine represented by formula (VIIIA) is used to one mole of the coupler represented by formula (IIA) to (VIIIA) and at least 4 equivalents, and preferably 4.4 to 20 equivalents of oxidizing agent is used. When X is not a hydrogen atom, the dye of formula (II) to (VII) can be synthesized by the same manner as above except that the amount of the oxidizing agent is at least 2 equivalents, and preferably 2.2 to 10 equivalents.

When the reaction is performed in an aqueous medium, the pH is higher than 8, and preferably the coupling reaction is performed in the pH range of from 10 to 12.

As the oxidizing agent, silver halide, hydrogen peroxide, manganese dioxide, potassium persulfate, oxygen, and other compounds described in Fieser and Fieser, *Organic Reagents*, can be used.

The dyes of this invention can be imagewise formed according to the process of silver halide color photography as described in U.S. Pat. No. 4,540,654.

For improving the stability of the dyes of this invention to light or heat, known stabilizers may be used together. Examples of organic compounds capable of improving the stability of the dyes are hydroquinone derivatives described in U.S. Pat. Nos. 3,935,016 and 3,982,944, hydroquinone diether derivatives described in U.S. Pat. No. 4,254,216 and Japanese Patent Application (OPI) No. 21004/80, phenol derivatives described in Japanese Patent Application (OPI) No. 145530/79, spiroindane derivatives and methylenedioxybenzene derivatives described in British Patent Application (OPI) Nos. 2,077,455 and 2,062,888, and Japanese Patent Application (OPI) No. 90155/86, chroman derivatives, spirochroman derivatives, and coumaran derivatives described in U.S. Pat. Nos. 3,764,337, 3,432,300, 3,574,627, and 3,573,050, Japanese Patent Application (OPI) Nos. 152225/77, 20327/78, 17729/78, and 90156/86, hydroquinone monoether derivatives and para-aminophenol derivatives described in Japanese Patent Application (OPI) No. 6321/80, British Patent 1,347,556, British Patent Application (OPI) No. 2,066,975, and Japanese Patent Publication No. 12337/79, and bisphenol derivatives described in Japanese Patent Publication No. 31625/73 and U.S. Pat. No. 3,700,455.

For improving the stability of the dyes to light or heat, the use of a metal complex together with the dye is also effective. Examples of such a meal complex are described in U.S. Pat. No. 4,245,018 and Japanese Patent Application (OPI) No. 97353/85.

Specific examples of the metal complex are illustrated below.

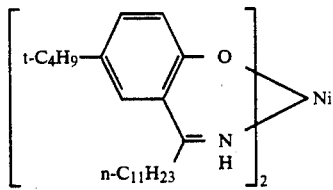

M-1

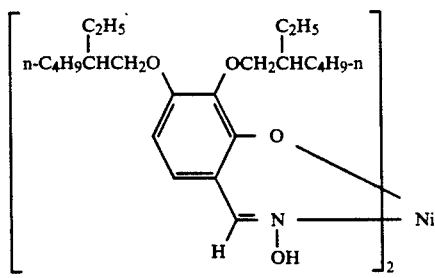

M-2)

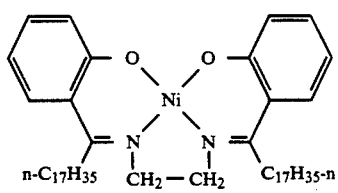

M-3)

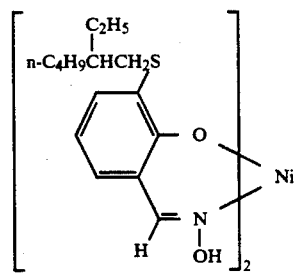

M-4)

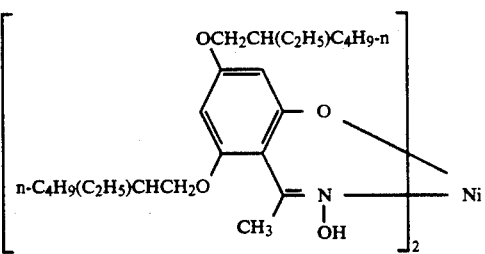

M-5)

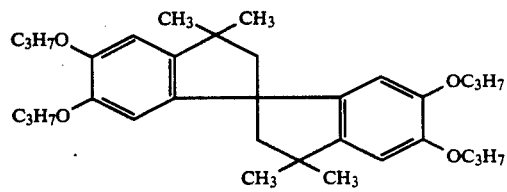

M-6)

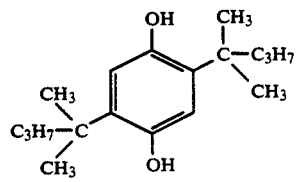

M-7)

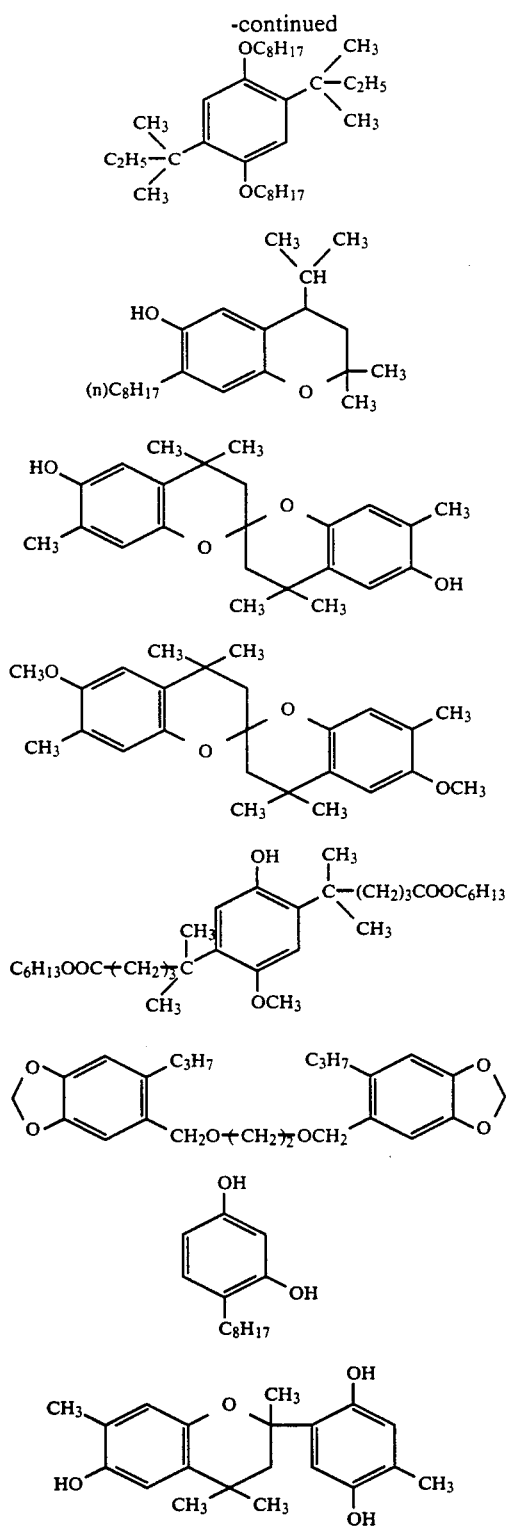

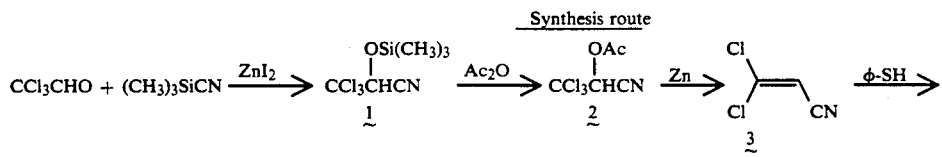

The pyrazoloazoleazomethine dyes of this invention represented by formula (I) described above are useful as magenta dyes or cyan dyes for forming color images. Also, the dyes of this invention are useful as magenta filter dyes or cyan filter dyes for silver halide color photographic materials and also useful as irradiation preventing dyes and antihalation dyes. Furthermore, the dyes of this invention are useful as magenta filter dyes or cyan filter dyes for solid pickup tubes.

The pyrazoloazoleazomethine dyes of this invention have far sharp visible absorption spectra as compared to conventional pyrazoloazoleazomethine dyes and hence give very clear hue. Also, the dyes of this invention have high molecular extinction coefficient and can give a desired optical density with a smaller amount thereof.

The following examples serve to illustrate the present invention in more detail without limiting, however, the scope thereof.

EXAMPLE 1

Synthesis of Compound 1

-continued
Synthesis route

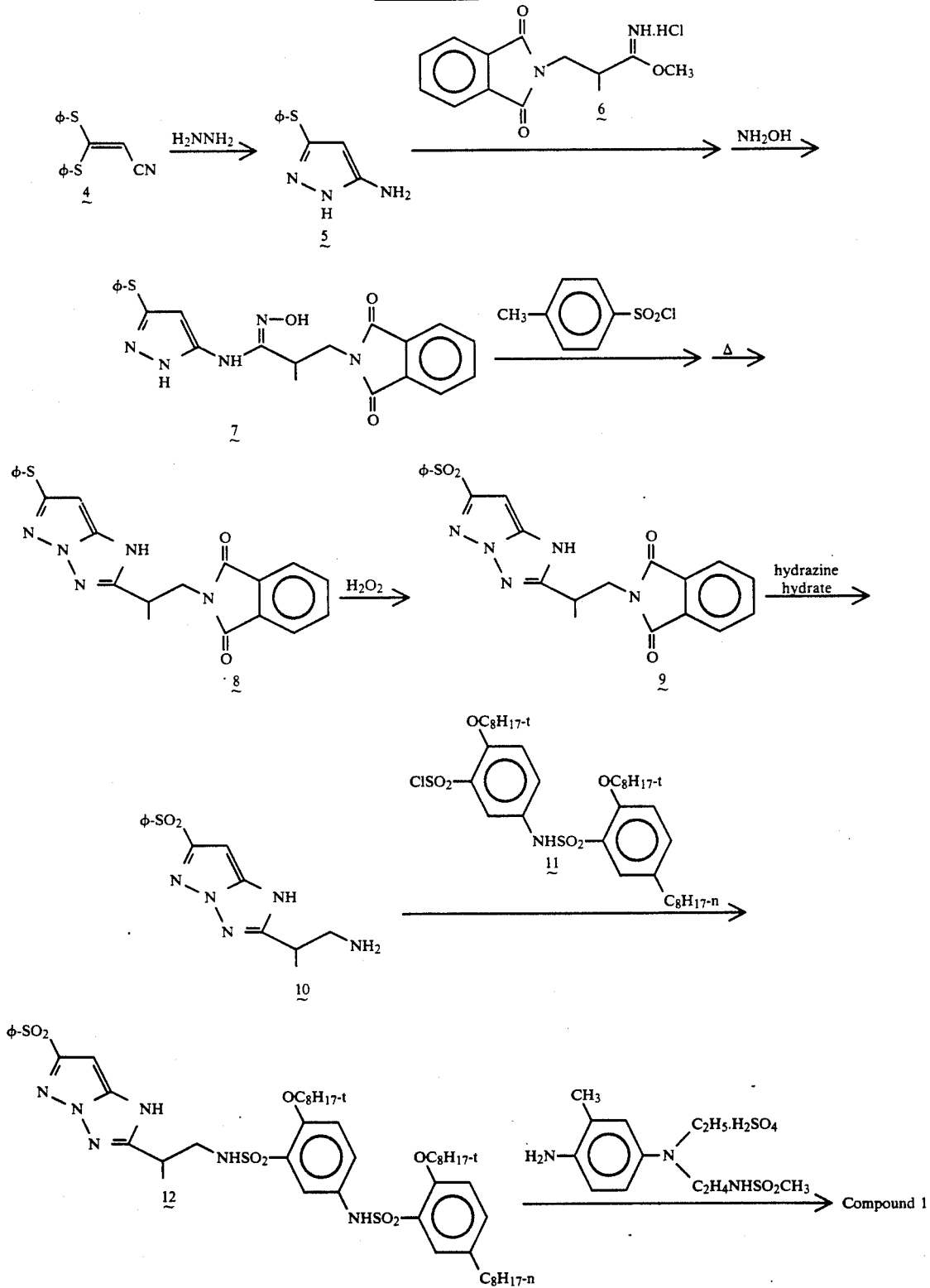

Synthesis of Intermediate 1

In a two liter three neck flask equipped with a dropping funnel and a stirrer were placed 116 g (0.79 mol) of chloral (reagent grade), 24 g (0.075 mol) of zinc iodide, and 1 liter of methylene dichloride, and the mixture was stirred at room temperature. Then, the mixture was cooled to a temperature of from 8° C. to 10° C. and 105 ml (0.75 mol) of methylsilylnitrile (reagent grade) was added dropwise to the mixture with stirring over a period of 30 minutes. The color of the mixture gradually changed form pink to brown. Thereafter, after further stirring the mixture for 3 hours at room temperature, insoluble matters were removed by filtration and the filtrate formed was distilled under reduced pressure. The $^1$H NMR spectra (solvent: CCl$_4$) of the liquid obtained showed $\delta=0.50$ ppm (belonging to Si (CH$_3$)$_3$ of Intermediate 1), $\delta=5.0$ ppm (belonging to methine of Intermediate 1), and $\delta=5.4$ ppm (belonging to methylene dichloride). From the NMR integral strength ratio, the content of Intermediate 1 was 69.1% by wight, the amount thereof was 173 g and the yield was 93%. ($\delta$represents a chemical shift value.)

Synthesis of Intermediate 2

In a one liter three neck flask equipped with a reflux condensor and a stirrer was placed 170 g (0.69 mol) of Intermediate 1 containing 76 g of methylene dichloride and after adding thereto 354 ml of acetic anhydride, the resultant mixture was heated to 125° to 130° C. for 9 hours with stirring. After cooling the mixture to room temperature, insoluble matters were filtered away, and the filtrate was distilled under reduced pressure. The residue thus formed was subjected to column chromatography using silica gel as a solid phase and chloroform as a moving phase, and the filtrate obtained was distilled under reduced pressure. Then, volatile matters were further distilled off at 100° C. using a vacuum pump. The $^1$H NMR spectra (solvent: CCl$_4$) of the liquid product thus obtained showed $\delta=2.1$ ppm (belonging to acetic anhydride), $\delta=2.3$ ppm (belonging to $-$OAc of Intermediate 2), and $\delta=6.0$ ppm (belonging to methine of Intermediate 2). From the integral strength ratio of the NMR, the content of Intermediate 2 was 95.6% by weight, the amount thereof was 98.1 g, and yield was 66%.

Synthesis of Intermediate 3

In a two liter three neck flask equipped with a reflux condensor and a stirrer was placed 98.1 g (0.45 mol) of Intermediate 2 containing 4.5 g of acetic anhydride and after adding thereto 400 ml of tetrahydrofuran, the mixture was heat-refluxed with stirring. Then, 32.5 g of zinc powder previously treated with hydrochloric acid was gradually added to the mixture with care. Thereafter, the mixture was heat-refluxed with stirring for 30 minutes and then distilled under reduced pressure. After removing 140 ml of the initial fraction, the residue was distilled at one stroke. The $^1$H NMR spectra (solvent: CCl$_4$) of the liquid product thus obtained showed $\delta=1.8$ ppm (belonging to tetrahydrofuran), $\delta=3.6$ ppm (belonging to tetrahydrofuran), and $\delta=6.1$ ppm (belonging to intermediate 3). From the integral strength ratio of the NMR, the content of Intermediate 3 was 20.9% by weight, the amount thereof was 36.6 g and the yield was 66%.

Synthesis of Intermediate 4

In a one liter three neck flask equipped with a stirrer were placed 25.8 g of sodium hydroxide and 150 ml of distilled water followed by stirring to dissolve sodium hydroxide. Then 69.6 g (0.60 mol) of thiopenol was dissolved in the solution with stirring and the solution obtained was ice-cooled, whereby the solution separated into two layers with white turbidity. While stirring the solution under ice-cooling 36.6 g (0.30 mol) of Intermediate 3 containing 138.5 g of tetrahydrofuran was added dropwise to the solution over a period of 30 minutes. Thereafter, the mixture was stirred for 6 hours at room temperature and allowed to stand overnight, whereby the solution separated into two layers. The lower layer was removed, the upper layer was placed in a separation funnel, and after adding thereto ethyl acetate and washing with an saturated aqueous solution of sodium chloride, the solution in the funnel was dried by Glauber's salt and distilled under reduced pressure. The residue was applied to column chromatography using silica gel as fixed phase and a mixture of ethyl acetate and n-hexane (1/10 by volume: the same hereinafter) as moving phase to provide 77.0 g (yield 95%) of oily Intermediate 4. The $^1$-NMR spectra (solvent: CCl$_4$) of the product showed $\delta=7.3$ ppm.

Synthesis of Intermediate 5

In a 500 milliliter three neck flask equipped with a reflux condenser and a stirrer was placed 77.0 g (0.285 mol) of Intermediate 4 and 173 ml of hydrazine hydrate and then the mixture was refluxed (inside temperature 110° to 115° C.) with heating - refluxing and stirring for 4 hours. In this case, the system was initially in two layers, but become one layer after reaction. After allowing to stand overnight, the reaction mixture was placed in a separation funnel, added with ethyl acetate, washed with a saturated aqueous sodium chloride solution containing 0.3 N sodium hydroxide, dried by Glauber's salt, and then purified by column chromatography using silica gel as fixed phase and a mixture of methanol and chloroform (1/5) as moving phase. Thus, 21.1 g (yield 39%) of light yellow oily Intermediate 5 was obtained.

The $^1$-NMR spectra (Solvent: (CD$_3$)$_2$CO, D: heavy hydrogenated acetone of the product showed $\delta=3.3$ ppm, $\delta=5.6$ ppm, $\delta=5.9$ ppm, and $\delta=7.2$ ppm.

Synthesis of Intermediate 7

In a 300 milliliter three neck flask equipped with a reflux condenser and a stirrer were placed 21.1 g (0.11 mol) of Intermediate 5, 200 ml of methanol and 37.3 g (0.13 mol) of Intermediate 6 prepared according to the method described in Japanese Patent Application (OPI) No. 171956/84 and then the mixture was stirred for 4 hours at room temperature. In this case, it was confirmed by thin layer chromatography that Intermediate 5 vanished. Thereafter, a solution of 115 g hydroxylamine hydrochloride and 13.5 g of sodium acetate dissolved in 50 ml of distilled water was added to the reaction mixture and the resultant mixture was heat-refluxed with stirring for 45 minutes. After cooling the mixture to room temperature, insoluble matters were filtered out, and the filtrate formed was distilled under reduced pressure. The residue was dissolved in ethyl acetate and the solution was washed with an aqueous 0.1 N sodium hydroxide solution, dried by Glauber's salt, and purified by column chromatography using silica gel as fixed phase and a mixture of ethyl acetate and benzene (1/1) as moving phase. Thus, 30.5 g (yield 66%) of light yellow oily Intermediate 7 was obtained.

Synthesis of Intermediate 8

In a 300 milliliter three neck flask equipped with a reflux condenser and a stirrer were placed 30.5 g (0.072 mol) of Intermediate 7, 50 ml of acetonitrile, 14.1 g of p-toluenesulfonyl chloride, and 5.9 ml of pyridine and the mixture was stirred for one hour under room temperature. The disappearance of the Intermediate 7 by the reaction was confirmed by thin layer chromatography. Thereafter, 110 ml of methanol and 5.9 ml of pyridine were added thereto and the resultant mixture was heat-refluxed with stirring for 2 hours. After adding thereto ethyl acetate, the mixture was washed with a saturated aqueous sodium chloride solution and supplied to column chromatography using silica gel as fixed phase and a mixture of ethyl acetate and benzene (1/1) as moving phase to concentrate the product, after then it was crystallized by the addition of n-hexane. Crystals Thus formed were filtered and dried to provide 6.6 g (yield 23%) of white crystals of Intermediate 8 having melting point of from 224° C. to 226° C. The mass spectrum thereof showed a parent peak: m/e=403.

Synthesis of Intermediate 9

In a 300 milliliter three neck flask equipped with a reflux condenser and a stirrer were placed 6.6 g (16.4 mmol) of Intermediate 8 and 100 ml of ethanol to form a suspension. While heat-refluxing the suspension with stirring, 0.10 g of NaWO$_4$·H$_2$O and 13.5 ml of an aqueous 35% hydrogen peroxide solution was added thereto and the mixture was further heat-refluxed with stirring for 2 hours. Then, the completion of the reaction was confirmed by thin layer chromatography. The reaction mixture was ice-cooled and crystals thus formed were collected by filtration, washed with ethanol, and then dried to provide 6.0 g (yield 84%) of the white crystals of Intermediate 9 having melting point of from 250° to 252° C. mass spectral parent peak: m/e=435.

Synthesis of Intermediate 10

In a 300 milliliter three neck flask equipped with a reflux condenser and a stirrer were placed 6.0 g (14 mmol) of Intermediate 9 and 100 ml of isopropyl alcohol and while heat-refluxing the mixture (suspension) with stirring, 1.0 g of hydrazine hydrate was added dropwise to the suspension. Thereafter, the mixture was heat-refluxed with stirring for 3 hours. The mixture was in the suspension state but the completion of the reaction was confirmed by thin layer chromatography. The reaction mixture was distilled under reduced pressure to remove the solvent, to form 6.6 g of solids. It was assumed that 4.2 g thereof was Intermediate 10 and 2.2 g thereof was phthalhydrazide.

Synthesis of Intermediate 12

In a 200 milliliter three neck flask equipped with a stirrer were placed 6.6 g of all of the aforesaid reaction mixture (i.e., Intermediate 10 and phthalhydrazide), 50 ml of N,N-dimethylacetamide, and 40 ml of tetrahydrofuran and the reaction mixture was dissolved in the solvent mixture. Then, 9.7 g (14 mmol) of Intermediate 11 prepared by an ordinary manner was added to the solution with stirring at room temperature and further a solution of 1.9 ml of triethylamine dissolved in 10 ml of tetrahydrofuran was added dropwise to the mixture over a period of 10 minutes. The resultant mixture was stirred for 30 minutes at room temperature. In this case, the disappearance of raw material of Intermediate 11 was confirmed by thin layer chromatography, but since raw material of Intermediate 10 remained, 1.9 g of Intermediate 11 and 0.4 ml of triethylamine were additionally added to the mixture. The resultant mixture was stirred for 2 hours at room temperature and the disappearance of Intermediate 10 was confirmed by thin layer chromatography. Then, after adding ethyl acetate, the reaction mixture was washed with a saturated aqueous sodium chloride solution of diluted hydrochloric acid, insoluble matter (presumed to be phthalhydrazide) was filtered away and the filtrate thus formed was purified by column chromatography using silica gel as fixed phase and a mixture of ethyl acetate and chloroform (1/5) as moving phase to provide 7.7 g (yield 57%) based on Intermediate 9) of the white crystals of Intermediate 12. The melting point thereof was from 87° C. to 94° C.

| | Elemental Analysis: | | |
|---|---|---|---|
| | H | C | N |
| Found: | 7.48% | 60.58% | 8.60% |
| Calculated: | 7.49% | 60.72% | 8.67% |

Mass spectrum parent peak: m/e=969=(M+H)$^+$.

Synthesis of Compound 1

In a 300 milliliter three neck flask equipped with a stirrer were placed 2.5 g (2.6 mmol) of Intermediate 12, 65 ml of chloroform, and 50 ml of distilled water and while stirring the mixture at room temperature, 3.75 g of sodium carbonate, 0.81 g of mono-sulfate of 4-amino-3-methyl-N-ethyl-N-($\beta$-methylsulfonamidoethyl)aniline (D20 described above as specific example of aromatic primary amine), and 1.65 g of ammonium persulfate were successively added to the mixture. The reaction mixture was colored in blue to blue-green. After stirring the mixture for one hour at room temperature, the upper layer (aqueous layer) thus formed was removed by decantation, and the lower layer was washed well with an aqueous dilute acetic acid solution, purified by column chromatography using silica gel as fixed phase and a mixture of methanol and chloroform (1/100) as moving phase, and further purified again by column chromatography using silica gel as fixed phase and a mixture of ethyl acetate and chloroform (2/5) as moving phase. After subjecting the product to distillation under reduced pressure to dryness, the product was further dried for 10 hours using a vacuum pump to provide 42.4 g (yield 75%) of amorphous Compound 1.

| | Elemental Analysis: | | |
|---|---|---|---|
| | H | C | N |
| Found: | 7.35% | 59.24% | 10.19% |
| Calculated: | 7.25% | 59.04% | 10.13% |

Mass spectrum parent peak: m/e=1235=(M+H)$^+$.

EXAMPLE 2

Comparison of Visible Absorption Spectra

In a 100 milliliter measuring flask was placed 2.00 mg of Compound 1 (molecular weight=1236.71) and after adding thereto ethyl acetate (high quality reagent) to dissolve the compound at room temperature, ethyl acetate was added up to the marked line. After light shaking the solution to form a homogeneous solution, the solution was placed in a quartz cell of 1 cm in thickness and the visible absorption spectrum thereof was measured by means of a ultraviolet visible ray spectrophotometer made by Shimazu Corporation.

Similarly, 3.00 mg of Comparison Compound A (molecular weight=1110.56) shown below described in Japanese Patent Application (OPI) No. 186567/85 was dissolved in ethyl acetate and the visible absorption spectra was measured by the same manner as above.

Comparison Compound A:

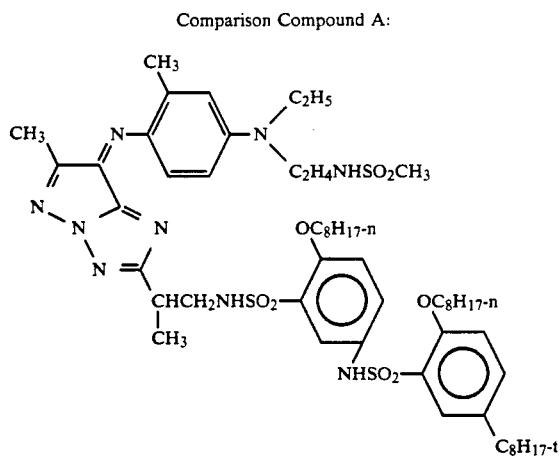

The visible absorption spectra of the both are shown in FIG. 1 so standardized that the maximum absorption intensity becomes 1. The solid line shows the visible absorption spectra of Compound 1 of this invention and the dotted line shows that of Comparison Compound A.

As is clear from FIG. 1, it can be seen that Compound 1 of this invention gives sharper absorption spectrum than Comparison Example A, and the hue of the former is far superior than the latter. Also, it can be seen that the maximum absorption of the compound of this invention is shifted to deep color side. That is, while Comparison Compound A shows magenta color, Compound 1 of this invention shows cyan color.

Furthermore, from the maximum absorption intensity and the mol density of each compound, the molecular extinction coefficient $\epsilon$ is calculated. These values are shown in Table 2.

EXAMPLE 3

Synthesis of Compound 2

By following the same synthesis route as in Example 1 using Intermediate 3 and trifluoromethane thiol, amorphous Compound 2 was obtained.

| | Elemental Analysis: | | | | | |
|---|---|---|---|---|---|---|
| | H | C | N | F | Cl | S |
| Found: | 6.53% | 53.47% | 8.33% | 5.50% | 3.45% | 9.61% |
| Calculated: | 6.68% | 53.08% | 8.44% | 5.72% | 3.56% | 9.66% |

Mass spectrum parent peak: $m/e = 995 = (M+H)^+$.

EXAMPLE 4

Comparison with Cyan Dye Formed from Known Cyan Coupler

By following the same procedure as in Example 1, cyan dyes (indoaniline dyes) D-3 and D-4 were prepared from cyan couplers C-3 disclosed in U.S. Pat. No. 3,772,002 and C-4 disclosed in U.S. Pat. No. 4,560,635, respectively, shown below.

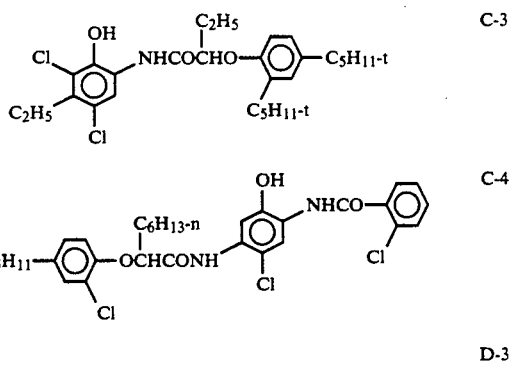

TABLE 2

| | Molecular Weight | Amount (mg) | Concentration (mol/l) | Maximum Absorp. Intensity | Molecular Extinction Coefficient $\epsilon$ $(l \cdot mol^{-1} \cdot cm^{-1})$ |
|---|---|---|---|---|---|
| Compound 1 of this Invention | 1236.71 | 2.00 | $1.62 \times 10^{-5}$ | 1.438 | $8.89 \times 10^4$ |
| Comparison Compound A | 1110.56 | 2.00 | $1.81 \times 10^{-5}$ | 1.005 | $5.58 \times 10^4$ |

From the results shown in the above table, it can be seen that Compound 1 of this invention has a significantly higher molecular extinction coefficient as compared to Comparison Compound A, and hence Compound 1 of this invention provides a desired optical density by a smaller amount thereof.

From the above-described results, it can be seen that when a particularly strong electron attractive group (the $\sigma_p$ value of benzenesulfonyl group which is a substituent of Compound 1 of this invention is 0.70, while the $\sigma_p$ value of the methyl group which is the substituent at the 6-position of Comparison Compound A is $-0.17$) is introduced to the substituent of the pyrazoloazole skeleton of the pyrazoloazoleazomethine dye, the maximum absorption wavelength is greatly shifted to a deep color side, the absorption thereof becomes sharper to make the hue clearer, and the molecular extinction coefficient becomes significantly larger.

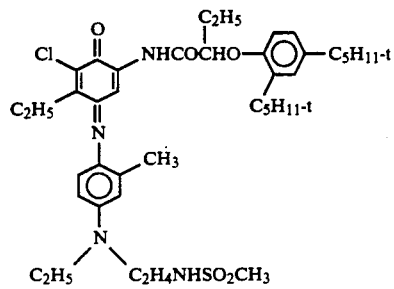

D-3

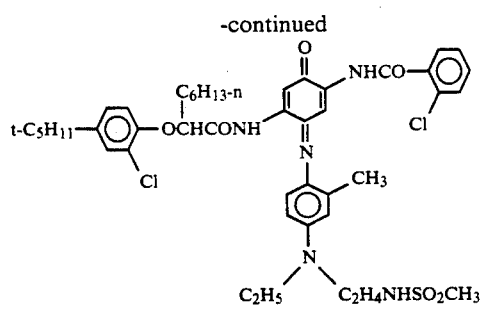

D-4

In the same manner as shown in Example 2, the visible absorption spectrum and the molecular extinction coefficient of each dye thus formed were measured, and they were compared with those of Compound 1 of this invention. The visible absorption spectra of these dyes are shown in FIG. 2, wherein the visible absorption spectrum of the Compound 1 of this invention is shown by solid line. As shown in FIG. 2, it can be seen that the absorption spectrum shown by Compound 1 of this invention is much sharper than comparison dyes D-3 and D-4, and that Compound 1 scarcely has an absorption in a blue region of from 400 n.m. to 500 n.m., hence, the hue of the dye of this invention is very clear cyan color in spite of the fact that the maximum absorption wavelength of Compound 1 of this invention is shorter than those of comparison dyes D-3 and D-4.

The data relating to the molecular extinction coefficients of these dyes are shown in Table 3.

TABLE 3

| | Molecular Weight | Amount (mg) | Concentration (mol/l) | Maximum Absorp. Intensity | Molecular Extinction Coefficient $\epsilon$ (l · mol$^{-1}$ · cm$^{-1}$) |
|---|---|---|---|---|---|
| Compound 1 of this Invention | 1236.71 | 2.00 | $1.62 \times 10^{-5}$ | 1.438 | $8.89 \times 10^4$ |
| Comparison Dye D-3 | 741.42 | 2.00 | $2.70 \times 10^{-5}$ | 0.661 | $2.45 \times 10^4$ |
| Comparison Dye D-4 | 852.91 | 2.00 | $2.34 \times 10^{-5}$ | 0.551 | $2.35 \times 10^4$ |

From the results shown in Table 3, it can be seen that Compound 1 of this invention gives a significantly higher molecular extinction coefficient as compared to comparison dyes D-3 and D-4.

From the results described above, it can be seen that the image-forming cyan dyes formed from the cyan coupler of this invention gives very sharp absorption spectrum as compared with cyan dyes formed from conventional phenolic cyan couplers and hence gives a clear cyan hue as well as showing a very high molecular extinction coefficient. Thereby a desired optical density can be obtained with a very small amount of the dye.

While the invention has been described in detail and with reference to specific embodiments thereof, it will be apparent to one skilled in the art that various changes and modifications can be made therein without departing from the spirit and scope thereof.

What is claimed is:

1. A polymer comprising a pyrazoloazoleazomethine dye of formula (I):

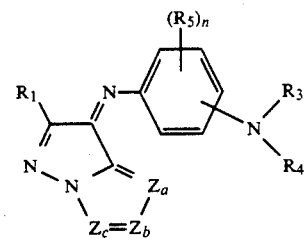

wherein, $R_1$ represents a substituent having a Hammett's substituent constant value of at least 0.6; $Z_a$, $Z_b$, and $Z_c$ each represents

wherein $R_2$ represents a hydrogen atom or a substituent, or =N—; when $Z_c=Z_b$ is a carbon-carbon double bond, it may form a part of an aromatic ring; $R_3$, $R_4$, and $R_5$ each represents a hydrogen atom or a substituent; and n represents 1 or 2; and wherein said dye is combined with the polymer through a divalent or higher valent group at $R_1$, $Z_a$, $Z_b$ or $Z_c$ wherein said polymer is a copolymer comprising ethylenically unsaturated monomers.

2. The polymer as in claim 1, wherein $R_5$ and

are the o- and p- position of the benzene ring, respectively.

3. The polymer as in claim 1, wherein the divalent linkage group is selected from group consisting of an alkylene group, a phenylene group, —NHCO—, —COHN—, —O—, —OCO— and an aralkylene group.

4. The polymer of claim 1, wherein the substituent represented by $R_1$ is a group selected from the group consisting of a cyano group, a nitro group, a trialkylammonium group, a trialammonium group, a dialkylsulfonium group, a diarylsulfonium group, a perfluoroalkylsulfinyl group, an ω-hydroperfluoroalkylsulfinyl group, an alkanesulfonyl group, an arylsulfonyl group, a β-carboxyvinyl group, and a β,β-dicyanovinyl group.

5. The polymer of claim 4, wherein the substituent represented by $R_1$ is a group selected from the group consisting of a trimethylaminoin group, a trifluoromethanesulfonyl group, a trifluoromethanesulfonyl group, a difluoromethanesulfonyl group, a methansesulfonyl group, a dichloromethanesulfonyl group, a pentafluoroethenaesulfonyl group, a dimethylsulfonium group, and a phenylsulfonyl group.

6. The polymer of claim 1, wherein $R_3$ and $R_4$ each represents a hydrogen atom or a substituted or unsubstituted alkyl group, and $R_5$ represents a hydrogen atom or a substituted or unsubstituted alkyl group.

7. The polymer of claim 6, wherein the substituent for the alkyl group represented by $R_3$, or $R_4$ is selected from the group consisting of a hydroxyl group, an alkoxy group, an alkoxyalkoxy group and an alkylsulfonamido group.

8. The polymer of claim 6, wherein the substituent for the alkyl group represented by $R_5$ is selected from the group consisting of an alkoxy group and a halogen atom.

9. The polymer as in claim 1, wherein the pyrazoloazoleazomethine dye is represented by the formula (II), (III), (IV), (V), (VI) or (VIII):

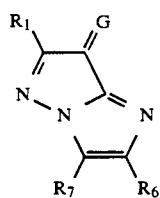
(II)

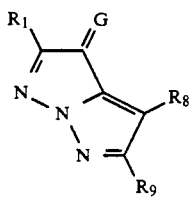
(III)

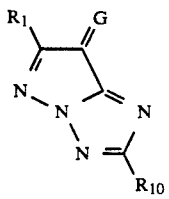
(IV)

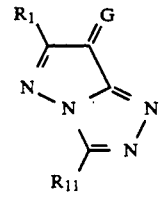
(V)

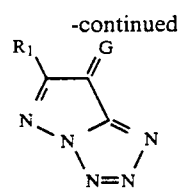
(VI)

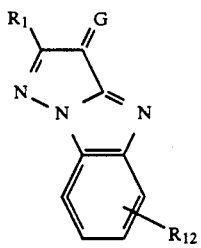
(VII)

wherein G represents a structural moiety represented by formula (VIII):

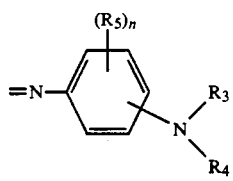
(VIII)

wherein $R_3$, $R_4$, $R_5$ and n have the same meanings as defined for formula (I); $R_1$ has the same meanings as defined for formula (I); $R_6$, $R_7$, $R_8$, $R_9$, $R_{10}$, $R_{11}$, and $R_{12}$ each represents a hydrogen atom or a substituent; and wherein said dye is bonded to a main chain of the polymer through a divalent or higher valent group at $R_1$, $R_6$, $R_7$, $R_8$, $R_9$, $R_{10}$, $R_{11}$ or $R_{12}$.

10. The polymer as in claim 9, wherein the pyrazoloazoleazomethine dye is represented by formula (IV), (V), or (VI).

11. The polymer as in claim 9, wherein the pyrazoloazoleazomethine dye is represented by formula (IV).

12. The polymer of claim 9, wherein said substituent represented by $R_6$, $R_7$, $R_8$, $R_9$, $R_{10}$, $R_{11}$ or $R_{12}$ each represents a hydrogen atom, a halogen atom, an alkyl group, an aryl group, a heterocyclic group, a cyano group, an alkoxy group an aryloxy group, an acylamino group, an anilino group, a ureido group, a sulfamoylamino group, an alkythio group, an arylthio group, an alkoxycarboynlamino group, a sulfonamide group, a carbamoyl group, a sulfamoyl group, a sulfonyl group, an alkoxycabonyl group, a heterocyclic oxy group, an acyloxy group, a carbamoyloxy group, a silyloxy group, an aryoxycabonylamino group, an imido group, a heterocyclic thio group, a sulfinul group, a phosphonyl group, an aryloxycarbonyl group or an acyl group.

* * * * *